(12) United States Patent
Nagasawa et al.

(10) Patent No.: US 9,817,314 B2
(45) Date of Patent: Nov. 14, 2017

(54) CONDUCTIVE POLYMER COMPOSITION, COATED ARTICLE, PATTERNING PROCESS, AND SUBSTRATE

(71) Applicant: SHIN-ETSU CHEMICAL CO., LTD., Tokyo (JP)

(72) Inventors: Takayuki Nagasawa, Jyoetsu (JP); Jun Hatakeyama, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/842,463

(22) Filed: Sep. 1, 2015

(65) Prior Publication Data
US 2016/0091792 A1    Mar. 31, 2016

(30) Foreign Application Priority Data
Sep. 30, 2014   (JP) .................................. 2014-201836

(51) Int. Cl.
| | | |
|---|---|---|
| G03F 7/004 | (2006.01) | |
| G03F 7/09 | (2006.01) | |
| C12P 13/04 | (2006.01) | |
| G03F 7/11 | (2006.01) | |
| G03F 7/20 | (2006.01) | |
| C07C 227/02 | (2006.01) | |
| C12P 13/08 | (2006.01) | |
| G03F 7/039 | (2006.01) | |
| C07C 229/06 | (2006.01) | |
| C08G 73/02 | (2006.01) | |

(52) U.S. Cl.
CPC ............ *G03F 7/093* (2013.01); *C07C 227/02* (2013.01); *C07C 229/06* (2013.01); *C08G 73/0266* (2013.01); *C12P 13/04* (2013.01); *C12P 13/08* (2013.01); *G03F 7/039* (2013.01); *G03F 7/11* (2013.01); *G03F 7/2059* (2013.01)

(58) Field of Classification Search
CPC . G03F 7/004; G03F 7/11; G03F 7/093; G03F 7/039; G03F 7/2059; C08G 73/0266; C08F 220/24; C07C 229/06; C07C 227/02; C12P 13/08; C12P 13/04
USPC ......... 430/270.1, 942, 322, 325, 329, 273.1; 252/500; 528/422; 564/1; 526/243; 562/553
See application file for complete search history.

(56) References Cited

U.S. PATENT DOCUMENTS

| | | | |
|---|---|---|---|
| 5,243,004 A * | 9/1993 | Funatsu .................. | H01B 1/122 526/256 |
| 5,370,825 A | 12/1994 | Angelopoulos et al. | |
| 5,766,515 A * | 6/1998 | Jonas ..................... | C08G 61/126 252/500 |
| 2003/0008247 A1 * | 1/2003 | Lelental .................... | B41M 5/44 430/517 |
| 2004/0191693 A1 * | 9/2004 | Takamiya ............. | B41C 1/1008 430/302 |
| 2008/0102407 A1 | 5/2008 | Ohsawa et al. | |
| 2008/0124292 A1 * | 5/2008 | Collin ..................... | A61K 8/361 424/70.7 |
| 2008/0145697 A1 | 6/2008 | Liu et al. | |
| 2008/0227296 A1 * | 9/2008 | So ............................ | C09G 1/02 438/692 |
| 2010/0055608 A1 | 3/2010 | Ohashi et al. | |
| 2011/0076464 A1 * | 3/2011 | Elschner ............. | H01L 51/0016 428/195.1 |
| 2012/0037594 A1 * | 2/2012 | Asakawa ............... | B82Y 10/00 216/41 |
| 2014/0038104 A1 * | 2/2014 | Bozano ................ | C09D 179/08 430/273.1 |

FOREIGN PATENT DOCUMENTS

| | | | |
|---|---|---|---|
| EP | 0041780 | A1 | 12/1981 |
| JP | H10-309449 | A | 11/1998 |
| JP | 2008108535 | A | 5/2008 |
| JP | 2008133448 | A | 6/2008 |
| JP | 2008147035 | A * | 6/2008 |
| JP | 2010-077404 | A | 4/2010 |
| JP | 2010-514161 | A | 4/2010 |
| JP | 2014-015550 | A | 1/2014 |

OTHER PUBLICATIONS

Machine translation of JP 2008-147035 (no date).*

* cited by examiner

*Primary Examiner* — Amanda C Walke
(74) *Attorney, Agent, or Firm* — Oliff PLC

(57) ABSTRACT

The present invention provides a conductive polymer composition which contains (A) a polyaniline-based conductive polymer having a repeating unit represented by the general formula (1), (B) a polyanion, and (C) an amino acid,

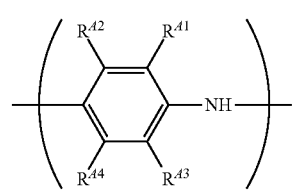

wherein $R^{41}$ to $R^{44}$ independently represent a hydrogen atom, a halogen atom, or a linear, branched, or cyclic monovalent hydrocarbon group having 1 to 20 carbon atoms and optionally containing a heteroatom; and $R^{41}$ and $R^{42}$, or $R^{43}$ and $R^{44}$ may be bonded to each other to form a ring. There can be provided a conductive polymer composition that has excellent antistatic performance and applicability, dose not adversely affect a resist, and can be suitably used in lithography using electron beam or the like.

10 Claims, No Drawings

CONDUCTIVE POLYMER COMPOSITION, COATED ARTICLE, PATTERNING PROCESS, AND SUBSTRATE

BACKGROUND OF THE INVENTION

Field of the Invention

The present invention relates to a conductive polymer composition containing a polyaniline-based conductive polymer, a coated article using the same, a patterning process, and a substrate. In particular, the present invention relates to a conductive polymer composition that is suitably used for prevention of electrification of a resist in lithography using ultraviolet light, electron beam, or the like, an article having an antistatic film formed by using the same, a patterning process using the conductive polymer composition, and a substrate obtained by the patterning process.

Description of the Related Art

Conventionally, in the fabrication process of a semiconductor device such as IC and LSI, microprocessing by lithography using a photoresist has been employed. This is a method of etching a substrate by using a resist pattern as a mask, in which the resist pattern is obtained by irradiating a thin film with light to induce crosslinking or decomposition reaction, thereby changing the solubility of the thin film, and subjecting the same to development treatment with a solvent or the like. In recent years, as a semiconductor device advances toward high integration, high-precision microprocessing using a beam with short wavelength have been required. The development of lithography using electron beam has been progressed for next generation technique because of its short-wavelength properties.

The lithography using electron beam has a specific problem of electrification phenomenon (charge-up) during exposure. This is a phenomenon that when a substrate to be irradiated with electron beam is coated with an insulating resist film, it is charged by accumulation of electric charge on or in the resist film. An orbit of incident electron beam is bent by the electrification, and therefore the precision of drawing is significantly reduced. Accordingly, an antistatic film to be applied on an electron beam resist has been investigated.

To control the reduction in drawing precision, Patent Document 1 discloses a composition containing a composite of an aniline-based conductive polymer and a polyacid, and $H_2O$; the composite of an aniline-based conductive polymer and a polyacid in amount of 5 to 10% by mass can readily form a film by spin coating, which exhibits sufficient antistatic effect with a film thickness of 150 nm, and this antistatic film can be removed and washed with $H_2O$.

However, when the antistatic film is formed on a chemically amplified resist, the shape or the sensitivity of the resist may change. For example, an acid produced by exposure is neutralized by a component in the antistatic film, whereby an exposed part of a positive resist is insolubilized during development, or an exposed part of a negative resist is partially dissolved during development. Otherwise, an acid component in the antistatic film makes an unexposed part of a positive resist partially soluble during development, or an unexposed part of a negative resist insoluble during development.

Since the chemically amplified resist does not have resistance to most organic solvent, an aqueous antistatic agent to be formed on the resist is often used. However, the surface of the chemically amplified resist is hydrophobic, so that the aqueous antistatic agent is unlikely to be applied. Therefore, it is necessary to add a surfactant or the like, but the addition of the surfactant may cause a mixing layer on the resist surface. In the mixing layer, the effect of an acid produced in the resist and an acid component in the antistatic film is enhanced after drawing, which leads to problems of changes in shape and sensitivity of the resist.

Patent Document 2 discloses a conductive composition containing a basic compound and a composite of a polyaniline-based conductive polymer substituted with an acidic group, and mentions the application to electrolytic capacitor, and an effect of enhancing the heat resistance and the conductivity under high-temperature atmosphere.

PRIOR ART DOCUMENTS

Patent Documents

[Patent Document 1] U.S. Pat. No. 5,370,825

[Patent Document 2] Japanese Patent Application Publication No. 2014-15550

[Patent Document 3] Japanese Patent Application Publication No. 2008-133448

[Patent Document 4] Japanese Patent Application Publication No. 2010-77404

SUMMARY OF THE INVENTION

The composition disclosed in Patent Document 1 has high acidity due to an acid derived from the polyacid in the composite of the polyaniline-based conductive polymer and the polyacid, so that although the antistatic effect is successful, there are unfavorable effects on lithography, such as changes in shape and sensitivity of the resist.

As to the polyaniline-based conductive polymer disclosed in Patent Document 2, which does not contain the polyacid described in Patent Document 1, the conductive polymer is limited to a self-doped polyaniline-based conductive polymer formed of aniline monomers to which an acidic substituent has been introduced, and thus the aniline-based conductive polymer does not form a composite with the polyacid. Moreover, the ratio of the acidic substituent on the aniline monomer to the amino group of the aniline is 1:1. From these reasons, it is difficult to change the composition ratio in the associate formed by the amino group and the acidic substituent in the polyaniline-based conductive polymer, according to use and purpose. In addition, since a restriction is made in proportion of the acidic group that does not participate in the composite formation, which significantly contributes to hydrophilicity of the polymer and to high dispersibility in $H_2O$, the polymer tends to reagglomerate in the composition, which causes problems such as defect occurrence when the composition is used for an antistatic film on the chemically amplified resist.

The present invention was made in view of the above circumstances, and an object thereof is to provide a conductive polymer composition that has excellent antistatic performance and applicability, does not adversely affect a resist, and in particular, can be suitably used in lithography using electron beam or the like.

To accomplish this object, the present invention provides a conductive polymer composition comprising: (A) a polyaniline-based conductive polymer having a repeating unit represented by the general formula (1); (B) a polyanion; and (C) an amino acid;

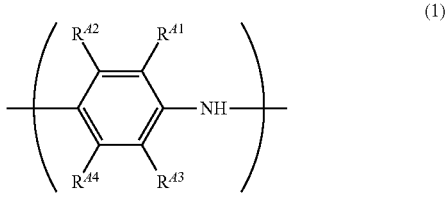

(1)

wherein $R^{41}$ to $R^{44}$ independently represent a hydrogen atom, a halogen atom, or a linear, branched, or cyclic monovalent hydrocarbon group having 1 to 20 carbon atoms and optionally containing a heteroatom; and $R^{41}$ and $R^{42}$, or $R^{43}$ and $R^{44}$ may be bonded to each other to form a ring.

Such a conductive polymer composition has excellent antistatic performance and applicability, and does not adversely affect a resist, so that it can be suitably used in lithography using electron beam or the like.

The component (C) is preferably represented by the general formula (2),

(2)

wherein $R^1$ and $R^2$ independently represent a hydrogen atom, a heteroatom, or a linear, branched, or cyclic monovalent hydrocarbon group having 1 to 20 carbon atoms and optionally containing a heteroatom; $R^3$ and $R^4$ independently represent a hydrogen atom or a linear, branched, or cyclic monovalent hydrocarbon group having 1 to 20 carbon atoms and optionally containing a heteroatom; $R^1$ and $R^3$, or $R^1$ and $R^4$ may be bonded to each other to form a ring; L represents a linear, branched, or cyclic tetravalent organic group having 1 to 20 carbon atoms and optionally containing a heteroatom; and when L contains a heteroatom, the heteroatom may be ion.

When the conductive polymer composition of the present invention contains the amino acid represented by the general formula (2) as the component (C), and an antistatic film is formed on a body to be processed by using the conductive polymer composition, acid diffusion between the body to be processed and the antistatic film is suppressed, whereby the effect of an acid can be reduced.

In this case, it is preferred that L in the general formula (2) of the component (C) be a linear, branched, or cyclic tetravalent organic group having 2 to 10 carbon atoms and optionally containing a heteroatom.

When the conductive polymer composition of the present invention contains such an amino acid as the component (C), and an antistatic film is formed on a body to be processed by using the conductive polymer composition, acid diffusion between the body to be processed and the antistatic film is further suppressed, whereby the effect of an acid can be further reduced.

The component (C) is preferably in an amount of 1 to 50 parts by mass based on 100 parts by mass of a composite of the component (A) and the component (B).

When the component (C) is in such an amount, acid diffusion from the antistatic film formed by using the conductive polymer composition to the resist layer is suppressed, so that the acid effect on lithography can be reduced while keeping the antistatic effect in electron beam-drawing. Therefore, a resist pattern with high resolution can be obtained. Likewise, this allows to give a resist body to be processed with little change in sensitivity over a period from film formation to pattern development.

Further, the component (C) is preferably in an amount of 3 to 10 parts by mass based on 100 parts by mass of a composite of the component (A) and the component (B).

When the component (C) is in such an amount, acid diffusion from the antistatic film formed by using the conductive polymer composition to the resist layer is further suppressed, so that the acid effect on lithography can be further reduced while keeping the antistatic effect in electron beam-drawing. Therefore, a resist pattern with higher resolution can be obtained. Likewise, this allows to give a resist body to be processed with further little change in sensitivity over a period from film formation to pattern development.

Also, it is preferred that the conductive polymer composition further comprise a nonionic surfactant.

Such a conductive polymer composition can be improved in wettability to a body to be processed such as substrate.

In this case, the nonionic surfactant is preferably in an amount of 1 to 50 parts by mass based on 100 parts by mass of a composite of the component (A) and the component (B).

Such a conductive polymer composition can be also improved in wettability to a resist surface, and has a sufficient antistatic performance.

The conductive polymer composition may be used for formation of an antistatic film.

The present invention also provides a coated article comprising an antistatic film formed by using the above-mentioned conductive polymer composition on a body to be processed.

An antistatic film formed from the conductive polymer composition of the present invention has excellent antistatic performance. Therefore, when such an antistatic film is used to coat various bodies to be processed, coated articles with high quality can be obtained.

In this case, the body to be processed may be a substrate having a chemically amplified resist film.

Since the conductive polymer composition of the present invention does not adversely affect a resist, the substrate having a chemically amplified resist film, which is unlikely to be applied conventionally, can be selected as the body to be processed on which an antistatic film formed from the conductive polymer composition of the present invention is to be provided.

In this case, the body to be processed may be the substrate for obtaining a resist pattern by pattern irradiation with electron beam.

The conductive polymer composition of the present invention can be suitably used in lithography using electron beam particularly, so that a resist pattern having high sensitivity, high resolution, and good pattern profile can be obtained.

Further, the present invention provides a patterning process comprising the steps of: forming an antistatic film on a chemically amplified resist film of a substrate having the chemically amplified resist film by using the above-mentioned conductive polymer composition; irradiating in a pattern with electron beam; and developing with an alkaline developer to obtain a resist pattern.

According to such a patterning process, electrification phenomenon during exposure can be prevented, and a resist pattern having high sensitivity, high resolution, and good pattern profile can be obtained.

Also, the present invention provides a substrate that has a resist pattern obtained by the above-mentioned patterning process.

The patterning process of the present invention can give a substrate that has a resist pattern with high sensitivity, high resolution, and good pattern profile.

As described above, since the conductive polymer composition of the present invention has excellent antistatic performance, it can be suitably used for prevention of electrification. Moreover, by coating various bodies to be processed with an antistatic film formed by using the conductive polymer composition of the present invention, coated articles with high quality can be obtained.

Also in application to lithography using photoresist, the conductive polymer composition of the present invention exhibits excellent applicability without adverse effects such as insolubilization of a resist and changes in sensitivity. Therefore, it can be suitably used, particularly, in lithography using electron beam or the like, and thereby a resist pattern having high sensitivity, high resolution, and good pattern profile can be obtained.

DETAILED DESCRIPTION OF THE PREFERRED EMBODIMENTS

Hereinafter, embodiments of the present invention will be described in detail, but the present invention is not limited to these embodiments.

As described above, in recent years, application of an antistatic film has been considered also in a production process of a semiconductor device. However, the conventional conductive composition and the like have problems, for example, an acid contained in the composition adversely affects a resist.

The present inventors have intensively investigated to solve the above-described problems, and consequently found that when an amino acid is used, a conductive polymer composition that has excellent antistatic performance and excellent applicability, does not adversely affect a resist, and can be suitably used in lithography using electron beam or the like can be obtained, thereby brought the present invention to completion.

That is, the conductive polymer composition of the present invention contains a polyaniline-based conductive polymer, a polyanion, and an amino acid.

Hereinafter, the present invention will be described in more detail.

[(A) Polyaniline-Based Conductive Polymer]

The conductive polymer composition of the present invention contains a polyaniline-based conductive polymer represented by the general formula (1), as component (A).

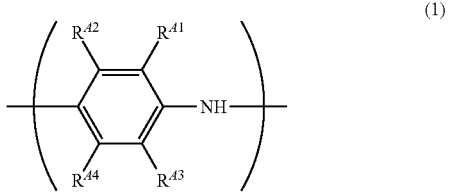

(1)

wherein $R^{41}$ to $R^{44}$ independently represent a hydrogen atom, a halogen atom, or a linear, branched, or cyclic monovalent hydrocarbon group having 1 to 20 carbon atoms and optionally containing a heteroatom; and $R^{41}$ and $R^{42}$, or $R^{43}$ and $R^{44}$ may be bonded to each other to form a ring.

The polyaniline-based conductive polymer is an organic polymer having a main chain composed of aniline or derivatives thereof other than para-substituted aniline. As a polymer having the similar functions, there may be mentioned polypyrroles, polythiophenes, polyacetylenes, polyphenylenes, polyphenylenevinylenes, polyacenes, polythiophenevinylenes, and copolymers thereof.

However, in view of high dispersibility in $H_2O$, dispersion filterability, peelability by $H_2O$ or an alkaline developer after film formation, low defectiveness in lithography, easy polymerization, low reagglomeration tendency during storage, and stability in air, the polyaniline-based conductive polymer is selected as component (A).

Even when the polyaniline-based conductive polymer is not substituted, sufficient conductivity can be achieved, however, introduction of substituent is more desirable in terms of high dispersibility in $H_2O$, low reagglomeration tendency, dispersion filterability, improved peelability by $H_2O$ or an alkaline developer after film formation, and reduction in defect in lithography. As the substituent, a functional group such as a halogen atom, an alkyl group, a carboxyl group, an alkoxy group, a hydroxyl group, and a cyano group may be introduced.

Illustrative examples of aniline monomers to be used for obtaining the polyaniline-based conductive polymer include aniline, 2-methyl aniline, 3-methyl aniline, 2-ethyl aniline, 3-ethyl aniline, 2-isopropyl aniline, 2-tert butyl aniline, 2,3-dimethyl aniline, 2,5-dimethyl aniline, 2,6-dimethyl aniline, 3,5-dimethyl aniline, 2,6-diethyl aniline, 2,6-diisopropyl aniline, 2,3,5,6-tetramethyl aniline, 2-methoxy aniline, 3-methoxy aniline, 2-ethoxy aniline, 3-ethoxy aniline, 3-isopropoxy aniline, 3-hydroxy aniline, 2,5-dimethoxy aniline, 2,6-dimethoxy aniline, 3,5-dimethoxy aniline, 2,5-diethoxy aniline, 2-methoxy-5-methyl aniline, 5-tert-butyl-2-methoxy aniline, 2-chloro-5-methyl aniline, 2-chloro-6-methyl aniline, 3-chloro-2-methyl aniline, and 5-chloro-2-methyl aniline. These monomers may be used singly or in combination of two or more kinds.

Among them, a (co)polymer composed of one kind or two or more kinds of monomers selected from 2-methyl aniline, 3-methyl aniline, 2-ethyl aniline, 3-ethyl aniline, 2-isopropyl aniline, 2-methoxy aniline, 3-methoxy aniline, 2-ethoxy aniline, 3-ethoxy aniline, 3-isopropoxy aniline, and 3-hydroxy aniline is preferably used in view of dispersibility in $H_2O$, conductivity, reactivity, and heat stability of the product when the co(polymer) is composited with a polyanion.

[(B) Polyanion]

The conductive polymer composition of the present invention contains a polyanion as component (B). The polyanion used in the conductive polymer composition of the present invention is a polymer having a plurality of anionic groups in one molecule, and can be obtained by a method of polymerizing a monomer having an anionic group or copolymerizing a monomer having an anionic group with a monomer having no anionic group. The monomers can be used singly or in combination of two or more kinds. Further, the polyanion can be also obtained by preparing a polymer having no anionic group, and then sulfonating the polymer with a sulfonating agent such as sulfuric acid, fuming sulfuric acid, and sulfamic acid. When a polymer having an anionic group is prepared, followed by sulfonation, a polyanion having anionic groups in higher content can be obtained.

Examples of the monomer constituting the polyanion used in the present invention include monomers containing a sulfonic acid group, a sulfonic acid group whose α-position is fluorinated, a phosphoric acid group, or a carboxyl group, more specifically, monomers containing a strong acidic group such as —O—SO$_3^-$H$^+$, —SO$_3^-$H$^+$, —CH(CF$_3$)—CF$_2$—SO$_3^-$H$^+$, —CF$_2$—SO$_3^-$H$^+$, —COO$^-$H$^+$, —O—PO$_4^-$H$^+$, and —PO$_4^-$H$^+$. Among them, —SO$_3^-$H$^+$, —CH(CF$_3$)—CF$_2$—SO$_3^-$H$^+$, —CF$_2$—SO$_3^-$H$^+$, and —COO$^-$H$^+$ are preferable in view of doping effect on the polyaniline-based conductive polymer. Further, it is preferable that the anionic groups be disposed in a main chain of the polyanion adjacently or at certain intervals.

Examples of the monomer containing a sulfonic acid group include styrene sulfonic acid, allyloxybenzene sulfonic acid, methallyloxybenzene sulfonic acid, vinyl sulfonic acid, allyl sulfonic acid, methallyl sulfonic acid, 2-(methacryloxy)ethane sulfonic acid, 4-(methacryloxy)butane sulfonic acid, isoprene sulfonic acid, 2-acrylamide-2-methylpropane sulfonic acid, 1,1,3,3,3-pentafluoro-2-methacryloyloxypropane-1-sulfonic acid, 1,1-difluoro-2-methacryloyloxyethane sulfonic acid, 1,1,3,3,3-pentafluoro-2-(4-vinyl-benzoyloxy)-propane-1-sulfonic acid, 1,1-difluoro-2-(4-vinyl-benzoyloxy)-ethane sulfonic acid, and benzyltrimethylammonium=2-methacryloyloxyethyl difluorosulfoacetate. These monomers may be used singly or in combination of two or more kinds.

Alternatively, the polyanion used in the present invention may be obtained by polymerizing polystyrene, polymethylstyrene, or the like, and sulfonating the polymer with a sulfonating agent such as sulfuric acid, fuming sulfuric acid, and sulfamic acid.

Patent Documents 3 and 4 have proposed an acid generator composed of a polymer type sulfonium salt capable of generating a sulfonic acid whose α-position is fluorinated. A sulfonium salt of an α-fluorinated sulfonic acid bonded to a polymer main chain is a superstrong acid, in which a sulfonic acid generated by photodecomposition of the sulfonium salt hardly diffuses. When this repeating unit is polymerized or copolymerized, the above-mentioned polyanion can be obtained. If the polymer type sulfonium salt is an alkali metal salt, an ammonium salt, an amine salt, or the like, it is preferable to make the solution thereof acidic by previously adding an inorganic acid such as sulfuric acid, hydrochloric acid, nitric acid, phosphoric acid, and perchloric acid or an organic acid, or using a cation exchange resin.

Examples of the monomer containing a phosphoric acid group include 3-chloro-2-acid phosphoxy propyl (meth)acrylate, acid phosphoxy polyoxyethylene glycol mono (meth)acrylate, mono(2-hydroxyethyl acrylate) acid phosphate, mono(2-hydroxyethyl methacrylate) acid phosphate, mono(2-hydroxypropyl acrylate) acid phosphate, mono(2-hydroxypropyl methacrylate) acid phosphate, mono(3-hydroxypropyl acrylate) acid phosphate, mono(3-hydroxypropyl methacrylate) acid phosphate, diphenyl-2-acryloyloxyethyl phosphate, and diphenyl-2-methacryloyloxyethyl phosphate. These monomers may be used singly or in combination of two or more kinds.

Examples of the monomer containing a carboxyl group include ethylenically unsaturated monocarboxylic acids such as acrylic acid, methacrylic acid, and crotonic acid; ethylenically unsaturated polyvalent carboxylic acids such as maleic acid, fumaric acid, and itaconic acid, and acid anhydrides thereof; and partially esterified products of an ethylenically unsaturated polyvalent carboxylic acid, such as methyl maleate and methyl itaconate. These monomers may be used singly or in combination of two or more kinds.

As the other monomer that has no anionic group and can be copolymerized with the anionic group-containing monomer, known compounds can be used without restriction. Examples thereof include conjugated diene monomers such as 1,3-butadiene, isoprene, 2-chloro-1,3-butadiene, and 2-methyl-1,3-butadiene; aromatic vinyl monomers such as styrene, α-methyl styrene, and p-methyl styrene; ethylenically unsaturated carboxylic acid alkyl ester monomers such as methyl (meth)acrylate, ethyl (meth)acrylate, butyl (meth)acrylate, and 2-ethylhexyl (meth)acrylate; ethylenically unsaturated carboxylic acid amide monomers such as acrylamide, methacrylamide, N,N-dimethylacrylamide, and N-methylolacrylamide; ethylenically unsaturated carboxylic acid hydroxyalkyl ester monomers such as hydroxyalkyl (meth)acrylate and glycerin di(meth)acrylate; carboxylic acid vinyl ester monomers such as vinyl acetate; (meth)acrylonitrile, N-vinylpyrrolidone, (meth) acryloylmorpholine, cyclohexylmaleimide, isopropylmaleimide, and glycidyl (meth)acrylate.

These monomers may be polymerized with an initiator to obtain the polyanion used in the present invention.

Moreover, the polyanion used in the present invention can also be obtained by sulfonation of polyether ketone (European Patent Application Publication No. 0041780(A1)), sulfonation of polyether ether ketone (Japanese Patent Laid-Open (kokai) No. 2008-108535), sulfonation of polyether sulfone (Japanese Patent Laid-Open (kokai) No. H10-309449), sulfonation of polyphenylene, polyfluorene, or polyvinyl carbazole (Japanese translation of PCT international application No. 2010-514161), sulfonation of polyphenylene oxide, and sulfonation of polyphenylene sulfide.

Among the polyanions, in view of solubility in a solvent and conductivity, polyisoprene sulfonic acid, a copolymer containing polyisoprene sulfonic acid, polysulfoethyl methacrylate, a copolymer containing polysulfoethyl methacrylate, poly(4-sulfobutyl methacrylate), a copolymer containing poly(4-sulfobutyl methacrylate), polymethallyloxybenzene sulfonic acid, a copolymer containing polymethallyloxybenzene sulfonic acid, polystyrene sulfonic acid, a copolymer containing polystyrene sulfonic acid, a copolymer containing poly-1,1,3,3,3-pentafluoro-2-methacryloyloxypropane-1-sulfonic acid, a copolymer containing poly-1,1-difluoro-2-methacryloyloxyethane sulfonic acid, a copolymer containing poly-1,1,3,3,3-pentafluoro-2-(4-vinyl-benzoyloxy)-propane-1-sulfonic acid, a copolymer containing poly-1,1-difluoro-2-(4-vinyl-benzoyloxy)-ethane sulfonic acid, a copolymer containing poly-2-methacryloyloxyethyl difluorosulfoacetate are preferred.

Among them, polystyrene sulfonic acid, poly-1,1,3,3,3-pentafluoro-2-methacryloyloxypropane-1-sulfonic acid, a copolymer containing poly-1,1-difluoro-2-methacryloyloxyethane sulfonic acid, a copolymer containing poly-1,1,3,3,3-pentafluoro-2-(4-vinyl-benzoyloxy)-propane-1-sulfonic acid, a copolymer containing poly-1,1-difluoro-2-(4-vinyl-benzoyloxy)-ethane sulfonic acid, poly-2-methacryloyloxyethyl difluorosulfoacetate, polysulfoethyl methacrylate, poly(4-sulfobutyl methacrylate) are more preferred.

The degree of polymerization of polyanion is preferably in the range of 10 to 100,000 monomer units, and in view of solubility in a solvent and conductivity, more preferably in the range of 50 to 10,000 monomer units. The molecular weight of the polyanion is preferably 5,000 to 1,000,000. When it is equal to or more than the lower limit, a solution in which the polyaniline-based conductive polymer is homogenized is easily obtained. When it is equal to or less than the upper limit, the conductivity is also improved.

In the conductive polymer composition according to the present invention, the polyanion is coordinated with the polyaniline-based conductive polymer to form a composite of the polyaniline-based conductive polymer and the polyanion.

(Method for Producing Composite of Polyaniline-Based Conductive Polymer and Polyanion)

The composite of the polyaniline-based conductive polymer and the polyanion can be obtained by, for example, adding a raw material monomer of the polyaniline-based conductive polymer to an aqueous solution of the polyanion or a water/organic solvent mixed solution of the polyanion, followed by adding an oxidizing agent to perform an oxidative polymerization. When the polyanion is in the form of an alkali metal salt, an ammonium salt, an amine salt, or the like, it is preferable to make the solution thereof acidic by previously adding an inorganic acid such as sulfuric acid, hydrochloric acid, nitric acid, phosphoric acid, and perchloric acid or an organic acid, or using a cation exchange resin.

Usable examples of the oxidizing agent and the oxidation catalyst include peroxodisulfate salts such as ammonium peroxodisulfate, sodium peroxodisulfate, and potassium peroxodisulfate, transition metal compounds such as ferric chloride, ferric sulfate, and cupric chloride, metal oxides such as silver oxide and cesium oxide, peroxides such as hydrogen peroxide and ozone, organic peroxides such as benzoyl peroxide, and oxygen.

As the reaction solvent to be used for the oxidative polymerization, water or a mixture of water and a solvent may be used. The solvent to be used here is miscible with water and preferably can dissolve or disperse the polyanion or the polyaniline-based conductive polymer as described below. Examples thereof include polar solvents such as N-methyl-2-pyrrolidone, N,N'-dimethylformamide, N,N'-dimethylacetamide, dimethyl sulfoxide, and hexamethyl phosphortriamide; alcohols such as methanol, ethanol, propanol, and butanol; aliphatic polyvalent alcohols such as ethylene glycol, propylene glycol, dipropylene glycol, 1,3-butylene glycol, 1,4-butylene glycol, D-glucose, D-glucitol, isoprene glycol, butanediol, 1,5-pentanediol, 1,6-hexanediol, 1,9-nonanediol, and neopentyl glycol; carbonate compounds such as ethylene carbonate and propylene carbonate; cyclic ether compounds such as dioxane and tetrahydrofuran; chain ethers such as dialkyl ether, ethylene glycol monoalkyl ether, ethylene glycol dialkyl ether, propylene glycol monoalkyl ether, propylene glycol dialkyl ether, polyethylene glycol dialkyl ether, and polypropylene glycol dialkyl ether; heterocyclic ring compounds such as 3-methyl-2-oxazolidinone; and nitrile compounds such as acetonitrile, glutaronitrile, methoxyacetonitrile, propionitrile, and benzonitrile. These solvents may be used singly or as a mixture of two or more kinds. The mixing ratio of the solvent that is miscible with water with respect to water is preferably 50% by mass or less of the whole reaction solvent.

The composite of the polyaniline-based conductive polymer and the polyanion thus obtained may be used after being pulverized by a homogenizer, a ball mill, or the like, if necessary.

For pulverization, a mixer/disperser which can apply a high shear force is preferably used. Illustrative examples of the mixer/disperser include a homogenizer, a high-pressure homogenizer, and a bead mill; among them, a high-pressure homogenizer is particularly preferable.

Illustrative examples of the high-pressure homogenizer include Nanomizer (trade name) manufactured by Yoshida Kikai Co., Ltd., Microfluidizer (trade name) manufactured by Powrex Corp., and Ultimizer manufactured by Sugino Machine Ltd.

As the dispersion treatment using the high-pressure homogenizer, there may be mentioned a treatment in which the composite solutions before the dispersion treatment are collided from the opposite direction with each other under high pressure, or a treatment in which the solution is passed through an orifice or a slit under a high pressure.

Before or after the pulverization, impurities may be removed by measures such as filtration, ultrafiltration, and dialysis; and also, purification may be done by using a cation exchange resin, an anion exchange resin, a chelate resin, or the like.

The total content of the polyaniline-based conductive polymer and the polyanion in the conductive polymer composition is preferably 0.05 to 10.0% by mass. When the total content of the polyaniline-based conductive polymer and the polyanion is 0.05% by mass or more, sufficient conductivity can be achieved. When it is 5.0% by mass or less, a uniform conductive coating film can be readily obtained.

The composite of the polyaniline-based conductive polymer and the polyanion generally shows a strongly acidic pH of 1 to 2.5 in the state of $H_2O$ dispersion unless the pH is adjusted. However, when it is used as an antistatic film to coat various bodies to be processed, the pH is preferably in the range of 4 to 8 considering the acid effect on an adjacent layer. When it is in the range of pH 4 to 8, corrosion due to an acid and acid diffusion to the adjacent layer are suppressed, and in the case that a resist is coated with the same, the resist is hardly damaged. Therefore, a further excellent pattern can be obtained after development.

The content of the polyanion preferably is such an amount that anionic groups in the polyanion is in the range of 0.1 to 10 mol, more preferably 1 to 7 mol, per 1 mol of the polyaniline-based conductive polymer. When the content of the anionic group in the polyanion is 0.1 mol or more, the doping effect on the polyaniline-based conductive polymer is high, and sufficient conductivity can be achieved. When the content of the anionic group in the polyanion is 10 mol or less, the content of the polyaniline-based conductive polymer is also appropriate, and sufficient conductivity can be achieved.

[(C) Amino Acid]

The conductive polymer composition of the present invention contains an amino acid as component (C).

In the present invention, any known amino acids may be used.

The amino acid may be used singly or in a mixture of two or more kinds.

The amino acid used in the present invention is preferably represented by the general formula (2),

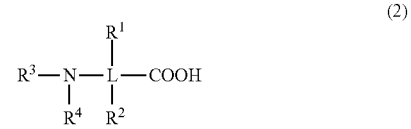

(2)

wherein $R^1$ and $R^2$ independently represent a hydrogen atom, a heteroatom, or a linear, branched, or cyclic monovalent hydrocarbon group having 1 to 20 carbon atoms and optionally containing a heteroatom; $R^3$ and $R^4$ independently represent a hydrogen atom or a linear, branched, or cyclic monovalent hydrocarbon group having 1 to 20 carbon atoms and optionally containing a heteroatom; $R^1$ and $R^3$, or $R^1$ and $R^4$ may be bonded to each other to form a ring; L represents a linear, branched, or cyclic tetravalent organic group having 1 to 20 carbon atoms and optionally containing a heteroatom; and when L contains a heteroatom, the heteroatom may be ion.
Illustrative examples of the structure of the amino acid represented by the general formula (2) are shown below.
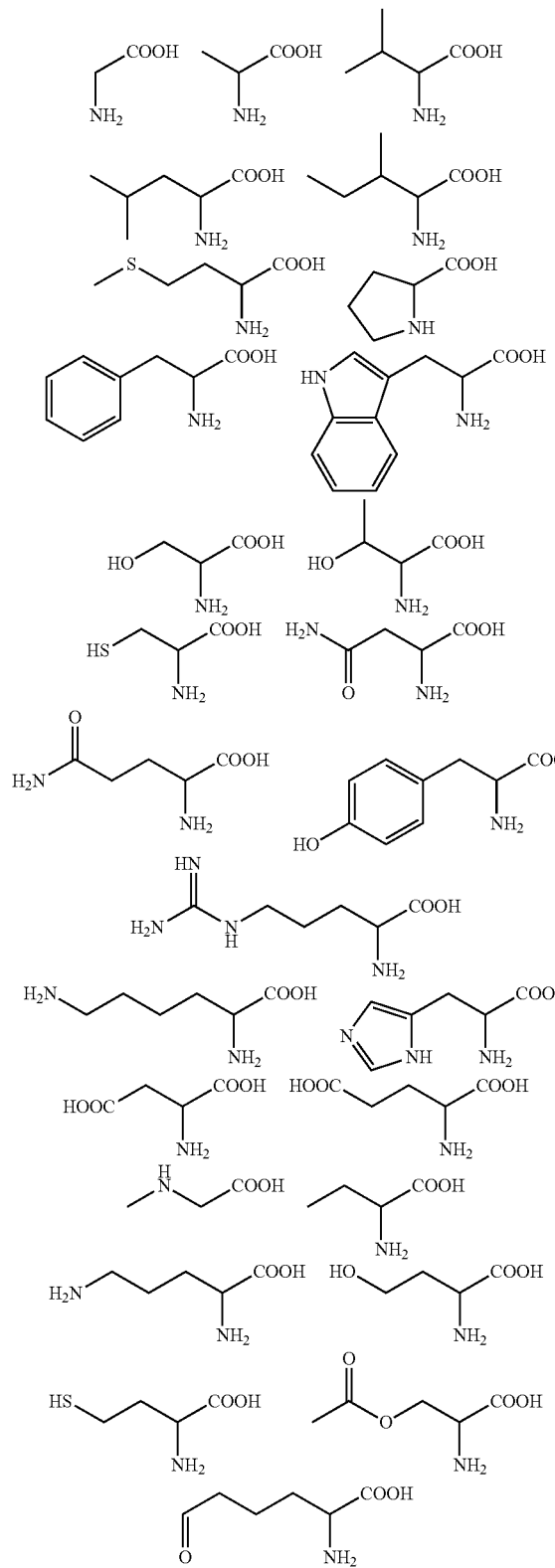
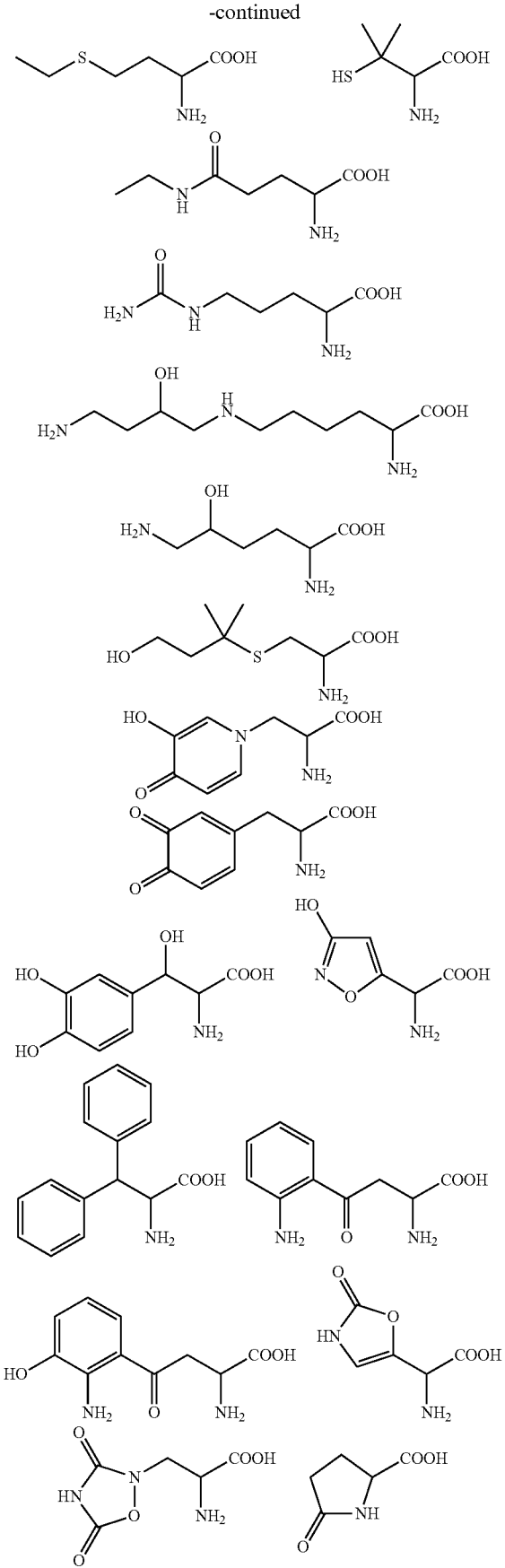

-continued

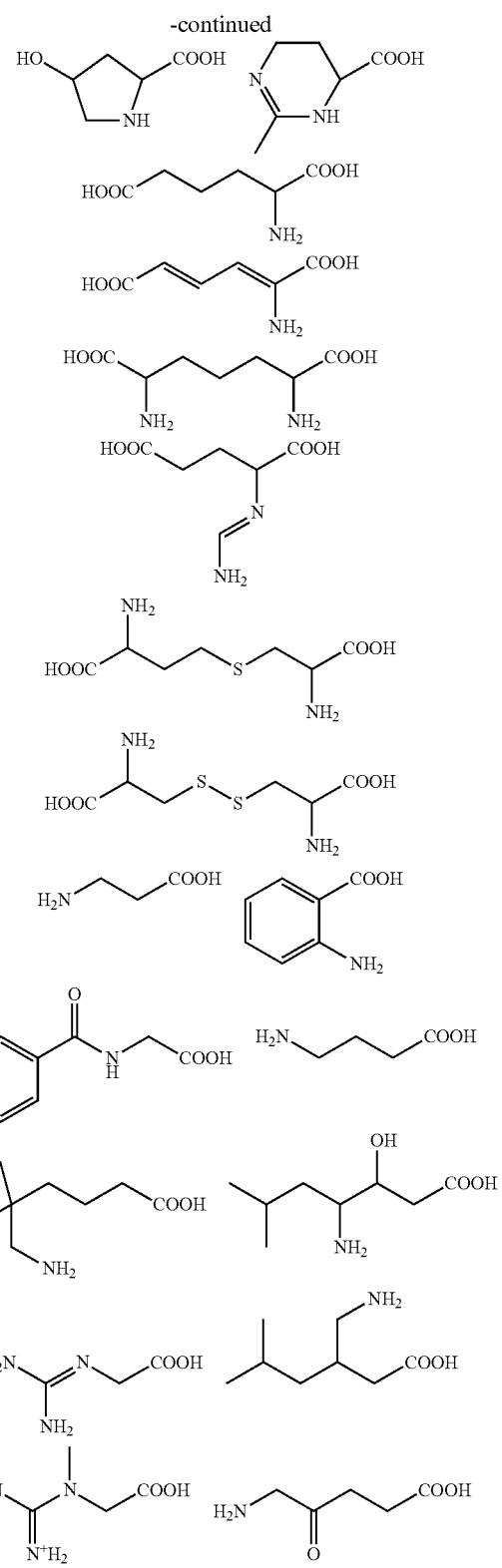

Also, the conductive polymer composition of the present invention preferably has a compound represented by the formula (2) wherein L is a linear, branched, or cyclic tetravalent organic group having 2 to 10 carbon atoms and optionally containing a heteroatom, as the amino acid of the component (C).

Other examples of the amino acid suitably used in the present invention other than the amino acid represented by the general formula (2) include the following compounds.

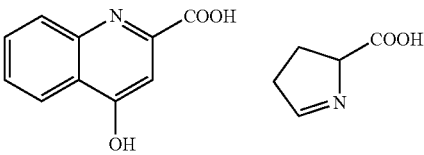

The content of the amino acid is preferably in the range of 1 to 50 parts by mass, more preferably 3 to 10 parts by mass based on 100 parts by mass of the composite of the polyaniline-based conductive polymer and the polyanion. When the amino acid is in such an amount, acid diffusion from the antistatic film formed by the conductive polymer composition of the present invention to the resist layer is suppressed, so that the effect of an acid on lithography can be reduced while keeping the antistatic effect in electron beam-drawing. Therefore, a resist pattern with higher resolution can be obtained. Likewise, this allows to give a resist body to be processed with little change in sensitivity over a period from film formation to pattern development.

(Surfactant)

In the present invention, a surfactant may be added to enhance the wettability to the body to be processed such as a substrate. As the preferable surfactant, there may be mentioned a nonionic surfactant. Illustrative examples thereof include polyoxyethylene alkyl ether, polyoxyethylene alkyl phenyl ether, polyoxyethylene carboxylic acid ester, sorbitan ester, polyoxyethylene sorbitan ester, and acetylene glycol.

The content of the nonionic surfactant is preferably in the range of 1 to 50 parts by mass, more preferably 2 to 20 parts by mass based on 100 parts by mass of the composite of the polyaniline-based conductive polymer and the polyanion. When it is equal to or more than the lower limit, wettability to the resist surface is further improved. When it is equal to or less than the upper limit, sufficient antistatic performance can be obtained.

The conductive polymer composition of the present invention can be obtained by, for example, mixing the composite of the polyaniline-based conductive polymer and the polyanion, a solvent, a surfactant, and so forth, followed by adding the amino acid to adjust the pH of the mixture, and if necessary, subjecting to a high-pressure homogenizer or the like, and filtrating the mixture through a UPE filter.

By applying the conductive polymer composition thus obtained to a body to be processed such as a substrate, an antistatic film can be formed. Examples of a method for applying the conductive polymer composition include coating by a bar coater or the like, spin coating, immersion, comma coating, spray coating, roll coating, and gravure printing. After the application, a heat treatment by a hot air circulating furnace, a hot plate, or the like is carried out to form an antistatic film.

Examples of the body to be processed include a glass substrate, a quartz substrate, a photomask blank substrate, a resin substrate, a silicon wafer, and a compound semiconductor wafer such as a gallium arsenic wafer and an indium phosphorus wafer.

Examples of a coated article that is coated with the antistatic film obtained from the conductive polymer composition of the present invention include a glass substrate having the antistatic film, a resin film having the antistatic film, and a resist substrate having the antistatic film.

In particular, since the conductive polymer composition of the present invention does not adversely affect a resist, a substrate having a chemically amplified resist film may be suitably used as the body to be processed. In addition, when the body to be processed is a substrate for obtaining a resist pattern by pattern irradiation with electron beam, more favorable results can be obtained.

Also, the present invention provides a patterning process comprising the steps of forming an antistatic film on a chemically amplified resist film of a substrate having the chemically amplified resist film by using the conductive polymer composition of the present invention; irradiating in a pattern with electron beam; and developing with an alkaline developer to obtain a resist pattern.

The patterning process can be performed in accordance with a conventional method except that the conductive polymer composition of the present invention is used, and the development may be performed after exposure followed by a heat treatment. Moreover, other steps such as etching, resist-removing, and washing may be also performed.

According to such a patterning process, electrification phenomenon during exposure can be prevented, and a resist pattern having high sensitivity, high resolution, and good pattern profile can be obtained.

Also, the present invention provides a substrate that has a resist pattern obtained by the above-mentioned patterning process.

The present invention is designed to be used for lithography using electron beam or the like, however, it can be also suitably used in lithography using ultraviolet light, or for preventing electrification of a film and glass because of excellent antistatic performance thereof.

EXAMPLES

Hereinafter, the present invention will be specifically described with reference to Production Examples, Examples, and Comparative Examples, but the present invention is not restricted to these examples.

A measurement method and an evaluation method of each physical property are as follows.

Antistatic films in Examples 1 to 10 and Comparative Examples 1 to 6 and underlying resist films were formed by spin coating with Spin coater MS-A200 (manufactured by Mikasa Co., Ltd.). As to a positive chemically amplified resist, a positive chemically amplified electron beam resist (a) available from Shin-Etsu Chemical Co., Ltd., was used. As to a negative chemically amplified electron beam resist, a material (b) available from Shin-Etsu Chemical Co., Ltd., was used.

The positive chemically amplified resist (a) and the negative chemically amplified resist (b) were baked in an accuracy incubator at 110° C. for 240 seconds to remove a solvent, thereby forming films. The antistatic films in Examples 1 to 10 and Comparative Examples 1 to 6 were formed by baking in an accuracy incubator at 90° C. for 90 seconds to remove a solvent. The thickness of the resist films and the antistatic films was measured by VASE (manufactured by J. A. Woollam Co., Inc.), a spectroscopic ellipsometer with a variable incident angle.

(Filterability)

After preparation of a conductive polymer composition in Examples and Comparative Examples, filtration was performed through a UPE filter having a pore diameter of 0.5 to 0.05 μm (manufactured by Entegris Inc.), thereby examining a pore diameter of the filter capable of filtrating the composition without clogging. The liquid-passing limits of the UPE filter through which the conductive polymer composition was filtrated in Examples 1 to 10 and Comparative Examples 1 to 6 are shown in Table 1.

(pH measurement)

The pH of the conductive polymer composition of Examples 1 to 10 and Comparative Examples 1 to 6 was measured with a pH meter D-52 (manufactured by HORIBA Ltd.). The results are shown in Table 1.

(Film Formability)

When the film could be formed uniformly, it was evaluated as "good", and when defect derived from particles or partial striation was generated in the film although refractive index could be measured, it was evaluated as "poor". These results are shown in Table 1.

(Peelability by Water Washing)

Onto the resist (a) or the resist (b) obtained by the film formation method as mentioned above, 10 μL of the conductive polymer composition was dropped, and the resist was heated in an accuracy incubator at 90° C. for 90 seconds, and left at room temperature for 2 minutes in air. The formed antistatic film was washed off with ion-exchanged water in a wash-bottle. When the antistatic film was peeled within 10 seconds, it was evaluated as "good", and when the antistatic film was peeled in more than 10 seconds and 20 seconds or less, it was evaluated as "moderate". As for the samples that could not be evaluated, reason was described. These results are shown in Table 1.

(Resist Damage)

With respect to the substrate after the evaluation of peelability by water washing, when the color of the resist portion exposed by peeling the antistatic film was not changed, it was evaluated as "good", when the color was partially changed, it was evaluated as "moderate" and when the color was completely changed, it was evaluated as "poor". These results are shown in Table 1.

(Surface Resistivity)

The surface resistivity (Ω/□) of the antistatic film was measured with Hiresta-UP MCP-HT450 and a J-Box, U-type probe, MCP-JB03 (both are manufactured by Mitsubishi Chemical corp.). These results are shown in Table 1.

(Electron beam lithography evaluation and PCD (Post Coating Delay) Evaluation)

The time-dependent change of the resist film before irradiation due to the conductive polymer film was measured. The two-layered film composed of the resist film and the conductive polymer film applied in accordance with the method described below was left in an electron beam-drawing apparatus for 7 days, 14 days, or 30 days right after film formation. Then, a resist pattern was formed by peeling process before or after PEB of the conductive polymer film as mentioned below. Thus, changes in pattern line width at the same sensitivity were examined, compared to the case where drawing was performed right after forming the resist film and the conductive polymer film.

Evaluation of Peeling Process Before PEB

A positive chemically amplified resist (a) was applied to a 6-inch silicon wafer by spin coating with MARK VIII (Coater/developer CLEAN TRACK, manufactured by Tokyo Electron Ltd.), and pre-baked at 110° C. for 240 seconds on a hot plate to prepare a resist film with a thickness of 150 nm. The conductive polymer composition was applied to the obtained wafer with the resist by spin coating using MARK VIII in the same manner as described above, and baked at 90° C. for 90 seconds on a hot plate to prepare a conductive polymer film. By using the wafer having the two-layered film composed of the resist film and the conductive polymer film, a resist pattern was formed right after the application or 7 days, 14 days, or 30 days after the application in the following manner. First, the wafer right after the application was exposed to light by using an electron beam exposure device (HL-800D manufactured by Hitachi High-Technologies Corporation, accelerating voltage: 50 keV). Then, the conductive polymer film was peeled by throwing pure water for 15 seconds, and the wafer was baked at 110° C. for 240 seconds (PEB: post exposure bake), and subjected to development with an aqueous solution of 2.38% by mass tetramethylammonium hydroxide. The produced wafer with a pattern was observed by a top-down SEM (scanning electron microscope). The exposure dose in which a 400-nm line and space is resolved at 1:1 is defined as optimal exposure dose (sensitivity) ($\mu C/cm^2$), and the minimum dimension in the optimal exposure dose is defined as a resolution. Similarly, a resist pattern was formed in the wafer left for 7 days, 14 days, or 30 days after the application, and changes in pattern line width were examined at the optimal exposure dose (sensitivity) ($\mu C/cm^2$) in which a 400-nm line and space is resolved at 1:1 in the wafer right after the application. The results are shown in Table 2.

Evaluation of Peeling Process after PEB

Similarly to the peeling process before PEB, a wafer having the two layered film composed of the resist film and the conductive polymer film was produced. The respective wafers left for 7 days, 14 days, or 30 days after the application were baked at 110° C. for 240 seconds (PEB: post exposure bake) without the steps of exposing to electron beam and peeling the conductive polymer film by throwing pure water for 15 seconds, and then subjected to development with an aqueous solution of 2.38% by mass tetramethylammonium hydroxide to obtain a resist pattern. Thus, changes in pattern line width were examined at the optimal exposure dose (sensitivity) ($\mu C/cm^2$) in which a 400-nm line and space is resolved at 1:1 in the wafer right after the application. The results are shown in Table 3.

Likewise, a negative resist (b) was subjected to the peeling process before PEB and the peeling process after PEB, and evaluated in the same manner as the positive resist (a). The results are shown in Tables 4 and 5.

Production Example 1

Synthesis of Polystyrene Sulfonic Acid 206 g of sodium styrene sulfonate was dissolved in 1,000 mL of ion-exchanged water. An oxidizing agent solution in which 1.14 g of ammonium persulfate had been previously dissolved in 10 mL of water was added dropwise thereto over 20 minutes under stirring at 80° C., and the solution was stirred for 2 hours.

To the obtained sodium styrene sulfonate-containing solution were added 1,000 mL of sulfuric acid diluted to 10% by mass and 10,000 mL of ion-exchanged water, and about 10,000 mL of the polystyrene sulfonic acid-containing solution was removed by ultrafiltration. To the residue was added 10,000 mL of ion-exchanged water, and about 10,000 mL of the solution was removed by ultrafiltration. This ultrafiltration operation was repeated 3 times.

Further, about 10,000 mL of ion-exchanged water was added to the obtained filtrate, and about 10,000 mL of the solution was removed by ultrafiltration. This ultrafiltration operation was repeated 3 times.

Water in the resultant solution was removed under reduced pressure to obtain solid colorless polystyrene sulfonic acid.

Conditions of the ultrafiltration were as follows (the same applied in other examples).

Cut-off molecular weight of the ultrafiltration membrane: 30 K
Cross-flow method
Flow rate of supply solution: 3,000 mL/min
Partial membrane pressure: 0.12 Pa Production Example 2

Synthesis of Polyaniline-Based Conductive Polymer Composite 27.3 g of 2-methoxyaniline was mixed with a solution in which 53.4 g of the polystyrene sulfonic acid obtained in Production Example 1 had been dissolved in 1,000 mL of ultrapure water at 25° C.

Into the resulting mixed solution was slowly added 45.8 g of ammonium persulfate dissolved in 200 mL of ultrapure water while stirring the mixed solution and keeping the temperature thereof at 0° C., to initiate reaction under stirring.

The obtained reaction solution was concentrated, and then added dropwise into 4,000 mL of acetone to obtain a green powder. The green powder was dispersed again into 1,000 mL of ultrapure water, and this dispersion was added dropwise into 4,000 mL of acetone to purify and recrystallize the green powder. This procedure was repeated 3 times. Then, the obtained green powder was redispersed in 2,000 mL of ultrapure water, and about 1,000 mL of water was removed by ultrafiltration. This procedure was repeated 10 times to obtain poly(2-methoxyaniline) doped with polystyrene sulfonic acid.

Example 1

11.5 g of a powder of the poly(2-methoxyaniline) doped with polystyrene sulfonic acid obtained in Production Example 2 was mixed with 354 g of ion-exchanged water, 0.28% by mass of L-(+)-Lysine (available from Tokyo Chemical Industry Co., Ltd.), and 0.05% by mass of SURFINOL465 (available from Nissin Chemical Industry Co., Ltd.). Then, the mixture was filtrated through a UPE filter subjected to hydrophilic treatment to prepare a conductive polymer composition.

Example 2

A conductive polymer composition was prepared in the same manner as in Example 1 except that L-(+)-Lysine was changed to 0.14% by mass.

Example 3

A conductive polymer composition was prepared in the same manner as in Example 1 except that L-(+)-Lysine was changed to 0.07% by mass.

Example 4

A conductive polymer composition was prepared by changing L-(+)-Lysine used in Examples 1 to 3 to L-Histidine (available from Tokyo Chemical Industry Co., Ltd.), and using the pH of the conductive polymer composition and the change in surface resistivity as an index. L-Histidine was added in amount of 0.14% by mass.

Example 5

A conductive polymer composition was prepared by changing L-(+)-Lysine used in Examples 1 to 3 to L-Histidine (available from Tokyo Chemical Industry Co., Ltd.), and using the pH of the conductive polymer composition and the change in surface resistivity as an index. L-Histidine was added in amount of 0.07% by mass.

Example 6

A conductive polymer composition was prepared by changing L-(+)-Lysine used in Examples 1 to 3 to L-Tryptophane (available from Tokyo Chemical Industry Co., Ltd.), and using the pH of the conductive polymer composition and the change in surface resistivity as an index. L-Tryptophane was added in amount of 0.38% by mass.

Example 7

A conductive polymer composition was prepared by changing L-(+)-Lysine used in Examples 1 to 3 to L-Tryptophane (available from Tokyo Chemical Industry Co., Ltd.), and using the pH of the conductive polymer composition and the change in surface resistivity as an index. L-Tryptophane was added in amount of 0.19% by mass.

Example 8

A conductive polymer composition was prepared by changing L-(+)-Lysine used in Examples 1 to 3 to Glycine (available from Tokyo Chemical Industry Co., Ltd.), and using the pH of the conductive polymer composition and the change in surface resistivity as an index. Glycine was added in amount of 0.28% by mass.

Example 9

A conductive polymer composition was prepared by changing L-(+)-Lysine used in Examples 1 to 3 to Glycine (available from Tokyo Chemical Industry Co., Ltd.), and using the pH of the conductive polymer composition and the change in surface resistivity as an index. Glycine was added in amount of 0.14% by mass.

Example 10

A conductive polymer composition was prepared by changing L-(+)-Lysine used in Examples 1 to 3 to L-Glutamine (available from Tokyo Chemical Industry Co., Ltd.), and using the pH of the conductive polymer composition and the change in surface resistivity as an index. L-Glutamine was added in amount of 0.27% by mass.

Comparative Example 1

A conductive polymer composition was prepared in the same manner as in Example 1 except using no amino acid.

Comparative Example 2

A conductive polymer composition was prepared by changing L-(+)-Lysine used in Examples 1 to 3 to 28% ammonia water (available from Kanto Chemical Co., Inc.), and using the pH of the conductive polymer composition and the change in surface resistivity as an index. The ammonia water was added in amount of 0.11% by mass.

Comparative Example 3

A conductive polymer composition was prepared by changing L-(+)-Lysine used in Examples 1 to 3 to Triisopropanolamine (available from Tokyo Chemical Industry Co., Ltd.), and using the pH of the conductive polymer composition and the change in surface resistivity as an index. Triisopropanolamine was added in amount of 0.35% by mass.

Comparative Example 4

A conductive polymer composition was prepared by changing L-(+)-Lysine used in Examples 1 to 3 to Triisopropanolamine (available from Tokyo Chemical Industry Co., Ltd.), and using the pH of the conductive polymer composition and the change in surface resistivity as an index. Triisopropanolamine was added in amount of 0.18% by mass.

Comparative Example 5

A conductive polymer composition was prepared by changing L-(+)-Lysine used in Examples 1 to 3 to an aqueous solution of Poly(ethyleneimine) (50% aqueous solution, available from Aldrich Co., Ltd.), and using the pH of the conductive polymer composition and the change in surface resistivity as an index. The aqueous solution of Poly(ethyleneimine) was added in amount of 0.48% by mass.

Comparative Example 6

A conductive polymer composition was prepared by changing L-(+)-Lysine used in Examples 1 to 3 to an aqueous solution of Poly(ethyleneimine) (50% aqueous solution, available from Aldrich Co., Ltd.), and using the pH of the conductive polymer composition and the change in surface resistivity as an index. The aqueous solution of Poly(ethyleneimine) was added in amount of 0.24% by mass.

The pore diameter of the filter, peelability by water washing, resist damage, pH, surface resistivity, and lithography evaluation in electron beam-drawing with respect to the antistatic films obtained from the conductive polymer compositions prepared in Examples and Comparative Examples are shown in Tables 1 to 5.

TABLE 1

|  | Filter (UPE μm) | Film formability | Peelability by water washing | Resist damage | pH | Surface resistivity (Ω/□) |
|---|---|---|---|---|---|---|
| Example 1 | 0.050 | good | good | good | 7.0 | 6.8E+08 |
| Example 2 | 0.050 | good | good | good | 5.1 | 3.2E+08 |

TABLE 1-continued

| | Filter (UPE μm) | Film formability | Peelability by water washing | Resist damage | pH | Surface resistivity (Ω/□) |
|---|---|---|---|---|---|---|
| Example 3 | 0.050 | good | good | good | 4.0 | 1.1E+08 |
| Example 4 | 0.050 | good | good | good | 5.2 | 4.9E+08 |
| Example 5 | 0.050 | good | good | good | 3.9 | 2.3E+08 |
| Example 6 | 0.050 | good | good | good | 4.1 | 6.5E+08 |
| Example 7 | 0.050 | good | good | good | 3.8 | 4.8E+08 |
| Example 8 | 0.050 | good | good | good | 3.9 | 5.5E+08 |
| Example 9 | 0.050 | good | good | good | 3.6 | 4.3E+08 |
| Example 10 | 0.050 | good | good | good | 3.6 | 6.2E+08 |
| Comparative Example 1 | 0.050 | good | good | good | 2.5 | 1.8E+08 |
| Comparative Example 2 | 0.100 | good | good | moderate | 6.0 (partially de-doped) | 5.6E+10 |
| Comparative Example 3 | 0.500 | good | good | moderate | 2.8 | 9.6E+09 |
| Comparative Example 4 | 0.500 | good | good | moderate | 2.6 | 7.5E+10 |
| Comparative Example 5 | 1.000 | poor | film formation failure | poor | 8.5 | not evaluable |
| Comparative Example 6 | 1.000 | poor | film formation failure | poor | 7.0 | not evaluable |

TABLE 2

Positive resist (a): peeling process before PEB, PCD

| | Change in PCD line width (nm) | | | |
|---|---|---|---|---|
| | Right after application | 7 days | 14 days | 30 days |
| Example 1 | 0 | −0.1 | −0.5 | −1.1 |
| Example 2 | 0 | −1.0 | −2.1 | −4.5 |
| Example 3 | 0 | −1.8 | −2.9 | −5.6 |
| Example 4 | 0 | −1.7 | −2.1 | −4.4 |
| Example 5 | 0 | −1.8 | −3.1 | −5.6 |
| Example 6 | 0 | −1.6 | −2.7 | −5.6 |
| Example 7 | 0 | −1.7 | −2.9 | −5.2 |
| Example 8 | 0 | −1.8 | −2.8 | −5.0 |
| Example 9 | 0 | −1.7 | −2.8 | −5.3 |
| Example 10 | 0 | −1.9 | −3.0 | −5.4 |
| Comparative Example 1 | 0 | −3.6 | −9.5 | −18.7 |
| Comparative Example 2 | 0 | −1.5 | −2.1 | −4.5 |
| Comparative Example 3 | 0 | −1.9 | −3.1 | −5.3 |
| Comparative Example 4 | 0 | −2.3 | −3.4 | −5.8 |
| Comparative Example 5 | not evaluable | not evaluable | not evaluable | not evaluable |
| Comparative Example 6 | not evaluable | not evaluable | not evaluable | not evaluable |

TABLE 3

Positive resist (a): peeling process after PEB, PCD

| | Change in PCD line width (nm) | | | |
|---|---|---|---|---|
| | Right after application | 7 days | 14 days | 30 days |
| Example 1 | 0 | −0.3 | −0.8 | −1.3 |
| Example 2 | 0 | −1.1 | −2.3 | −4.8 |
| Example 3 | 0 | −1.9 | −2.8 | −5.9 |
| Example 4 | 0 | −1.9 | −2.2 | −4.4 |
| Example 5 | 0 | −1.9 | −3.2 | −5.8 |
| Example 6 | 0 | −1.8 | −2.8 | −5.9 |
| Example 7 | 0 | −1.8 | −2.9 | −5.1 |
| Example 8 | 0 | −2.1 | −2.8 | −5.3 |
| Example 9 | 0 | −1.8 | −3.0 | −5.4 |
| Example 10 | 0 | −2.2 | −3.2 | −5.5 |
| Comparative Example 1 | 0 | −3.8 | −9.9 | −22.0 |
| Comparative Example 2 | 0 | −1.9 | −2.3 | −5.4 |
| Comparative Example 3 | 0 | −2.8 | −3.0 | −5.0 |
| Comparative Example 4 | 0 | −2.8 | −3.5 | −5.5 |
| Comparative Example 5 | not evaluable | not evaluable | not evaluable | not evaluable |
| Comparative Example 6 | not evaluable | not evaluable | not evaluable | not evaluable |

TABLE 4

Negative resist (b): peeling process before PEB, PCD

| | Change in PCD line width (nm) | | | |
|---|---|---|---|---|
| | Right after application | 7 days | 14 days | 30 days |
| Example 1 | 0 | 0.2 | 0.6 | 1.3 |
| Example 2 | 0 | 1.1 | 2.2 | 4.3 |
| Example 3 | 0 | 3.3 | 5.3 | 9.8 |
| Example 4 | 0 | 1.4 | 3.3 | 7.5 |
| Example 5 | 0 | 3.7 | 6.5 | 11.0 |
| Example 6 | 0 | 2.5 | 5.4 | 12.3 |
| Example 7 | 0 | 3.2 | 5.2 | 13.1 |
| Example 8 | 0 | 2.5 | 4.8 | 11.4 |
| Example 9 | 0 | 3.0 | 5.4 | 12.3 |
| Example 10 | 0 | 3.7 | 5.5 | 12.4 |
| Comparative Example 1 | 0 | 7.5 | 13.7 | 21.4 |
| Comparative Example 2 | 0 | 1.3 | 2.8 | 5.0 |
| Comparative Example 3 | 0 | 6.0 | 10.3 | 15.4 |

TABLE 4-continued

Negative resist (b): peeling process before PEB, PCD

| | Change in PCD line width (nm) | | | |
|---|---|---|---|---|
| | Right after application | 7 days | 14 days | 30 days |
| Comparative Example 4 | 0 | 6.1 | 10.5 | 15.4 |
| Comparative Example 5 | not evaluable | not evaluable | not evaluable | not evaluable |
| Comparative Example 6 | not evaluable | not evaluable | not evaluable | not evaluable |

TABLE 5

Negative resist (b): peeling process after PEB, PCD

| | Change in PCD line width (nm) | | | |
|---|---|---|---|---|
| | Right after application | 7 days | 14 days | 30 days |
| Example 1 | 0 | 0.2 | 0.8 | 1.5 |
| Example 2 | 0 | 1.2 | 2.3 | 4.5 |
| Example 3 | 0 | 3.7 | 5.6 | 10.2 |
| Example 4 | 0 | 1.5 | 3.5 | 7.8 |
| Example 5 | 0 | 4.0 | 6.4 | 11.4 |
| Example 6 | 0 | 2.5 | 5.3 | 12.5 |
| Example 7 | 0 | 3.3 | 5.9 | 13.6 |
| Example 8 | 0 | 2.6 | 5.1 | 11.9 |
| Example 9 | 0 | 3.2 | 5.5 | 12.6 |
| Example 10 | 0 | 3.9 | 5.7 | 12.5 |
| Comparative Example 1 | 0 | 8.0 | 14.0 | 21.8 |
| Comparative Example 2 | 0 | 1.4 | 2.6 | 5.1 |
| Comparative Example 3 | 0 | 6.0 | 10.5 | 15.5 |
| Comparative Example 4 | 0 | 6.3 | 10.9 | 16.0 |
| Comparative Example 5 | not evaluable | not evaluable | not evaluable | not evaluable |
| Comparative Example 6 | not evaluable | not evaluable | not evaluable | not evaluable |

As shown in Table 1, Examples 1 to 10, which used the conductive polymer compositions of the present invention, not only could control the increase in surface resistivity after film formation, but also increase the pH, compared with Comparative Example 1, which used the composition having no amino acid. Thus, these compositions could function as an antistatic film during irradiation with electron beam, and suppress the acid effect on the resist film.

On the other hand, Comparative Example 1, which used the composition having no amino acid, was excellent in antistatic effect, but exhibited low pH, so that an acid in the composition readily diffused to the resist, and adversely affected the resist pattern. Comparative Examples 2 to 6, which were expected to improve pH, caused the phenomenon of deteriorating the conductive polymer composition, so that discoloration and precipitation occurred, and the surface resistivity was increased. Therefore, these samples did not serve as a composition to be applied on a resist for providing an antistatic film for the electron beam resist.

Moreover, as shown in Tables 2 to 5, also in the evaluation of lithography using electron beam, the samples that used the antistatic film obtained from the conductive polymer composition of the present invention (Examples 1 to 10) showed excellent sensitivity, little sensitivity change, and excellent resolution and pattern profile. In the PCD evaluation, higher pH indicates better result, which facilitates adjustment of the storage stability of articles coated with the resist and the conductive polymer film (antistatic film) while considering the value of surface resistivity. On the other hand, Comparative Example 1, which used the composition having no amino acid, was excellent in antistatic effect, but exhibited low pH as mentioned above. As regards the PCD, Comparative Example 1 exhibited significantly large change width, so that it got the problem of storage stability of articles coated with the resist and the conductive polymer film. Comparative Examples 2 to 6 were inferior in stability of the conductive polymer film (antistatic film) itself, and the resist film was damaged due to the acid effect. In addition, since these conductive polymer film have high surface resistivity, the antistatic effect could not be sufficiently obtained.

It should be noted that the present invention is not limited to the foregoing embodiment. The embodiment is just an exemplification, and any examples that have substantially the same feature and demonstrate the same functions and effects as those in the technical concept described in claims of the present invention are included in the technical scope of the present invention.

What is claimed is:

1. A conductive polymer composition comprising: (A) a polyaniline-based conductive polymer having a repeating unit represented by the general formula (1); (B) a polyanion; (C) an amino acid; (D) water or solvent; and a nonionic surfactant;

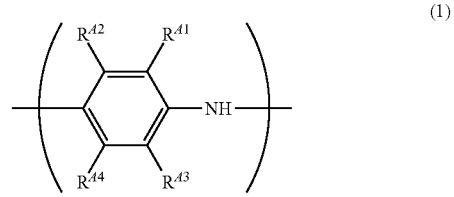

wherein $R^{41}$ to $R^{44}$ independently represent a hydrogen atom, a halogen atom, or a linear, branched, or cyclic monovalent hydrocarbon group having 1 to 20 carbon atoms and optionally containing a heteroatom; and $R^{41}$ and $R^{42}$, or $R^{43}$ and $R^{44}$ may be bonded to each other to form a ring, wherein component (C) is selected from the group consisting of the amino acids shown below:

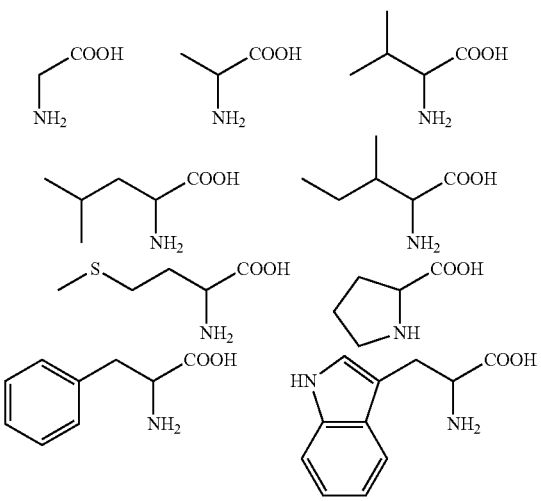

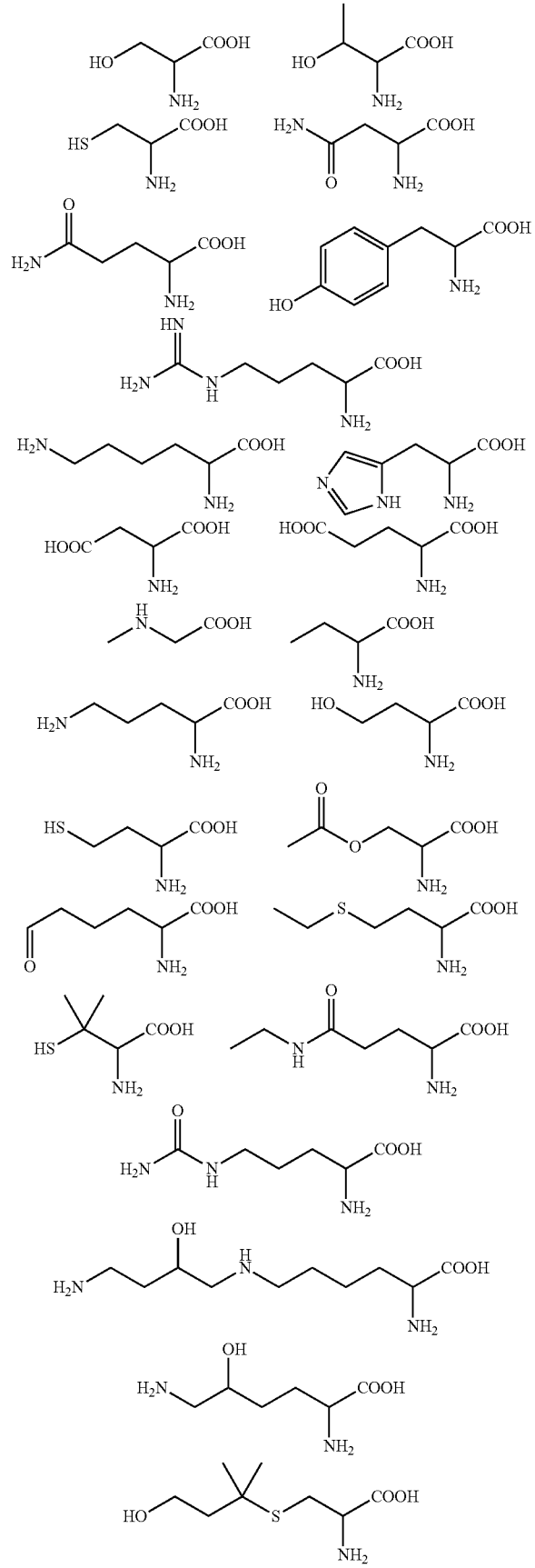
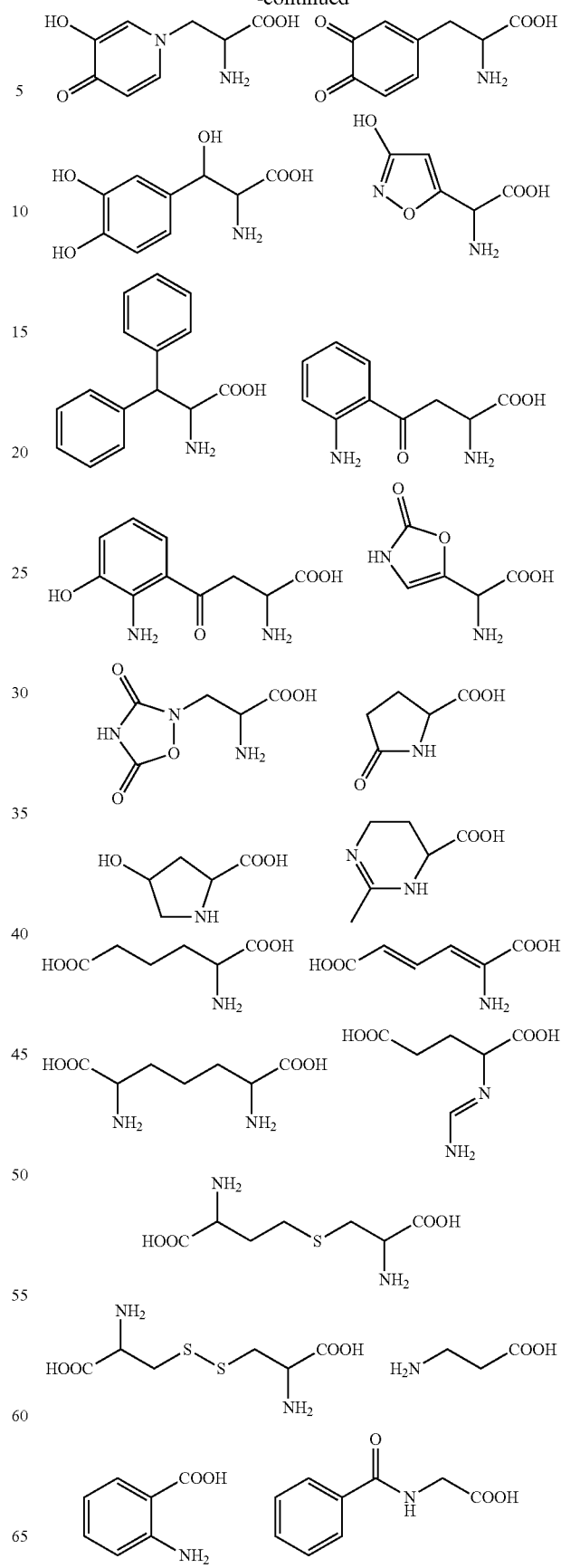

-continued

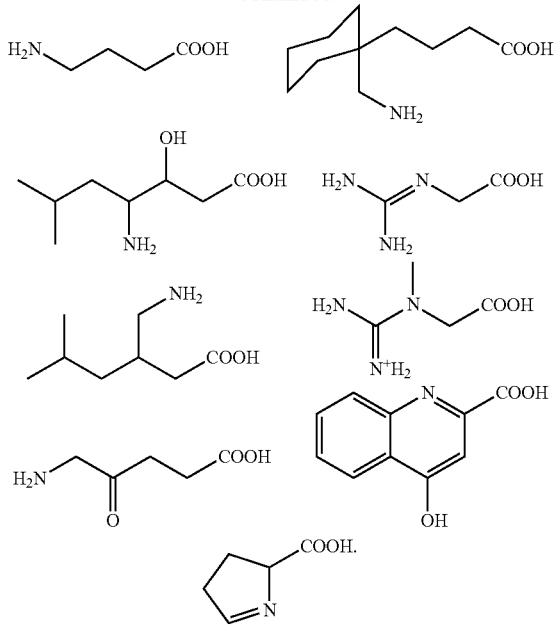

2. The conductive polymer composition according to claim 1, wherein the component (C) is in an amount of 1 to 50 parts by mass based on 100 parts by mass of a composite of the component (A) and the component (B).

3. The conductive polymer composition according to claim 1, wherein the component (C) is in an amount of 3 to 10 parts by mass based on 100 parts by mass of a composite of the component (A) and the component (B).

4. The conductive polymer composition according to claim 1, wherein the nonionic surfactant is in an amount of 1 to 50 parts by mass based on 100 parts by mass of a composite of the component (A) and the component (B).

5. An antistatic film formed using the conductive polymer composition according to claim 1.

6. A coated article comprising:
a body to be processed; and
an antistatic film formed on the body to be processed using the conductive polymer composition according to claim 1.

7. The coated article according to claim 6, wherein the body to be processed is a substrate having a chemically amplified resist film.

8. The coated article according to claim 7, wherein the substrate is configured so that a resist pattern is formed on the substrate when the substrate is exposed to pattern irradiation with an electron beam.

9. A patterning process comprising the steps of:
providing a substrate having a chemically amplified resist film;
forming an antistatic film on a chemically amplified resist film using the conductive polymer composition according to claim 1;
irradiating in a pattern with electron beam; and
developing with an alkaline developer to obtain a resist pattern.

10. A substrate that has a resist pattern obtained by the patterning process according to claim 9.

* * * * *